United States Patent [19]

Hillstead

[11] Patent Number: 5,066,285
[45] Date of Patent: Nov. 19, 1991

[54] CATHETER INTRODUCER SHEATH MADE OF EXPANDED POLYTETRAFLUOROETHYLENE

[75] Inventor: Richard A. Hillstead, Miramar, Fla.
[73] Assignee: Cordis Corporation, Miami Lakes, Fla.
[21] Appl. No.: 470,716
[22] Filed: Jan. 26, 1990
[51] Int. Cl.⁵ .............................................. A61M 5/178
[52] U.S. Cl. ................................. 604/164; 604/264; 604/280; 128/772
[58] Field of Search ............... 604/167, 164, 171, 244, 604/264, 175, 280; 128/772

[56] References Cited

U.S. PATENT DOCUMENTS

| | | |
|---|---|---|
| 3,953,566 | 4/1976 | Gore . |
| 4,000,739 | 1/1977 | Stevens ........................ 604/167 |
| 4,082,893 | 4/1978 | Okita . |
| 4,149,535 | 4/1979 | Volder ........................ 604/164 |
| 4,187,390 | 2/1980 | Gore . |
| 4,488,877 | 12/1984 | Klein et al. .................... 604/244 |
| 4,781,693 | 11/1988 | Martinez et al. ................ 604/175 |
| 4,850,975 | 7/1989 | Furukawa . |

OTHER PUBLICATIONS

Article Entitled, Physical Properties and Test Methods for Expanded Polytetrafluoroethylene (PTFE) Grafts, by Michael E. McClurken, Ph.D., James M. McHaney and William M. Colone, pp. 82–94.

Primary Examiner—Stephen C. Pellegrino
Assistant Examiner—Michael Rafa
Attorney, Agent, or Firm—Gerstman & Ellis, Ltd.

[57] ABSTRACT

A catheter introducer comprises a tubular sheath for inserting and guiding a catheter into living tissue. In accordance with this invention, the sheath is typically made of expanded polytetrafluoroethylene, with a result that the catheter introducer sheath is highly flexible and non-kinking, but it also exhibits relatively high hoop strength so that burrs, notching, and kinking can be avoided as the catheter introducer is advanced through tissue while surrounding a dilator unit, to achieve advantages not found in prior art analogs.

7 Claims, 2 Drawing Sheets

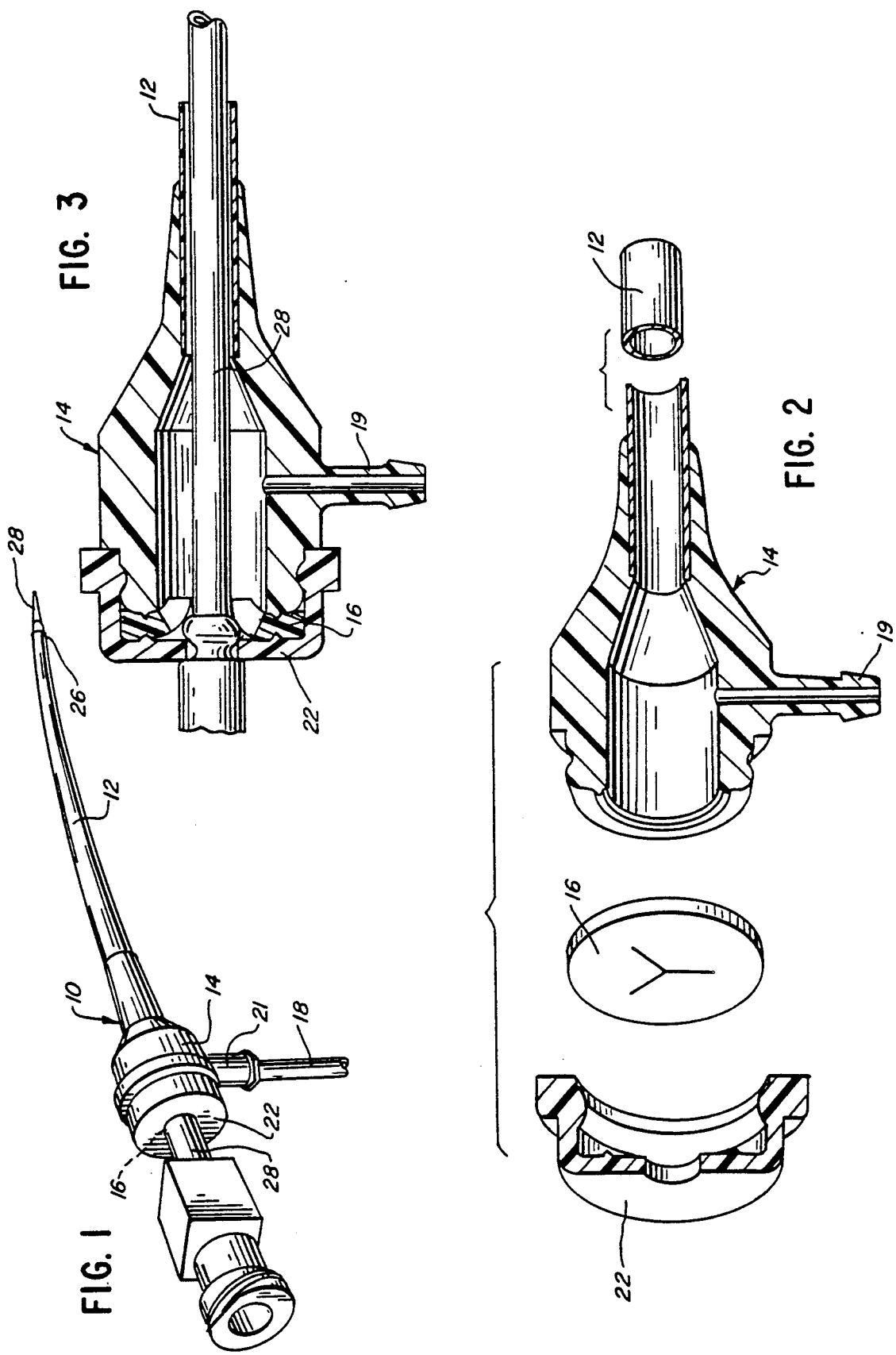

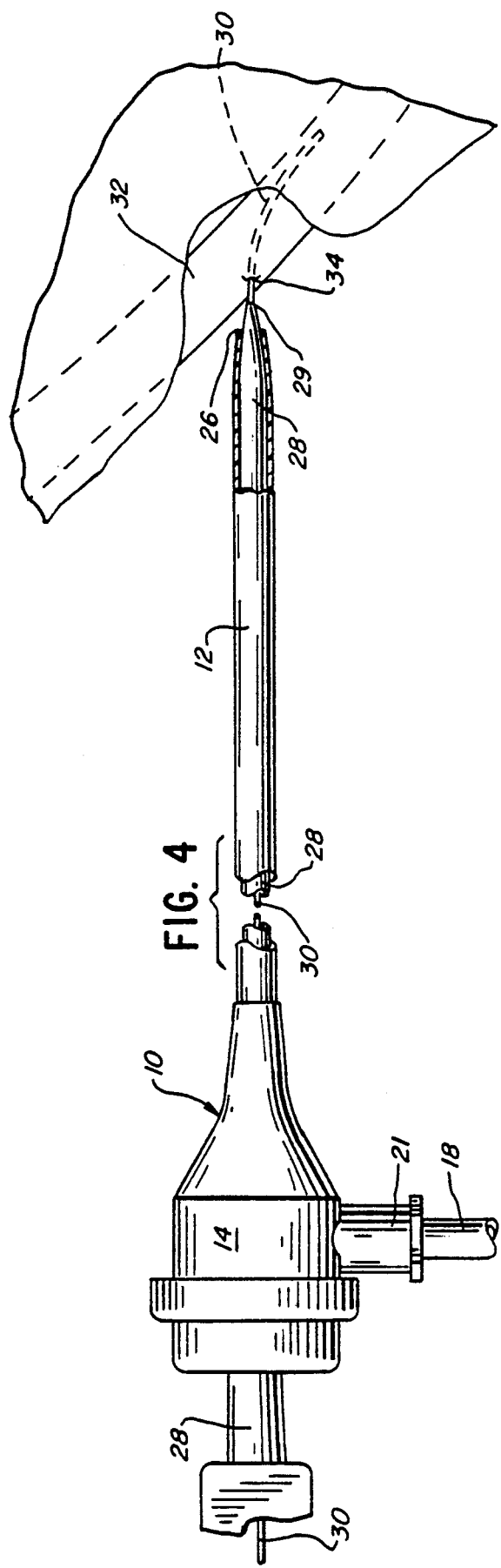
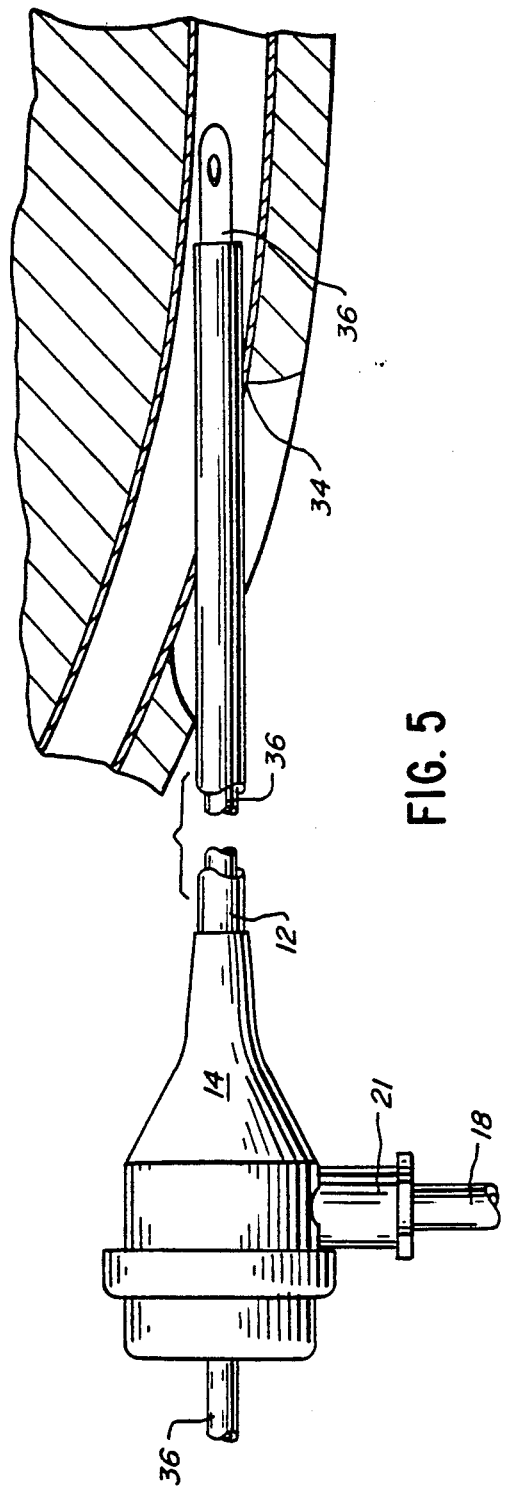

CATHETER INTRODUCER SHEATH MADE OF EXPANDED POLYTETRAFLUOROETHYLENE

BACKGROUND OF THE INVENTION

Intravascular catheters such as angiographic catheters are introduced from the exterior of a patient into an artery or vein. After such introduction, the catheter is advanced and maneuvered through the arteriovenous system to a desired site, which may be an area of arterial stenosis, or an area from which x-ray contrast media is injected into the system, or the interior of the heart itself, for example. As described for example in Stevens U.S. Pat. No. 4,000,739, such catheter may be emplaced by first inserting a hollow needle with a trocar through the skin into the lumen of the desired blood vessel. Following this, a guide wire is passed through the needle and advanced up the artery or vein toward the area or the organ to be studied. The needle can then be removed, leaving the guide wire in the vessel.

Following this, a catheter introducer comprising a tubular sheath and a removable, hollow stylet or dilator unit may be advanced together over the wire into the vessel. Then, the guide wire and the dilator unit are removed, leaving only the sheath of the catheter introducer member present in the vessel.

Then, the desired catheter can be advanced through the sheath into the vessel.

The sheath of the catheter introducer typically carries a hub with hemostasis valve means on its proximal end to avoid uncontrolled bleeding and air embolism. The dilator unit, and then the catheter, pass through this hemostasis valve, the design of which is well-known and currently in commercial use.

As described for example in Furukawa et al. U.S. Pat. No. 4,850,975 a problem exists in the conventional technology of catheter introducers, in that the sheath which surrounds the dilator unit is subject to kinking, burring, or notching. One example of this is particularly illustrated in FIG. 11 of the Furukawa et al. patent, in which the distal end of the thin catheter introducer sheath is shown to be drawn away from intimate engagement with the dilator unit by the mechanical action of sheath advancement or the like. This happens because the sheath is desirably made as thin as possible, and, in the prior art, the sheath is typically made of a plastic which is only partially flexible to achieve self supporting characteristics, and thus is subject to kinking if it is bent unduly without internal support. Also, "burrs" can form on the proximal edge of the catheter introducer sheaths of the prior art, as described in the Furukawa et al. patent. Such burrs or irregularities, if formed in the catheter introducer sheath, can damage blood vessel linings or the like, and are quite undesirable.

However, sheaths made of more flexible elastomers or the like to avoid kinking would lack desired hoop strength, and thus would be even less useful.

As shown in FIG. 12 of the Furukawa et al. patent, another attempted prior art solution to avoid such burring and the like is to simply thicken the wall of the catheter introducer sheath and to bevel its proximal end. However, this also has its significant disadvantages, chiefly the fact that it is important for the sheath to be of a minimum thickness. An increased sheath thickness of course expands the puncture hole in the blood vessel and makes hemostasis more difficult.

The suggested solution of the Furukawa et al. patent includes the use of a dilator unit which defines a longitudinal slit to provide transverse elastic deformation action to the dilator unit. This, however, requires the use of a dilator unit that is more expensive to manufacture, and it exhibits other disadvantages that have restricted the commercial use of the Furukawa et al. invention.

The notching, kinking, or burring that takes place at the distal tip of the catheter introducer sheath occurs most frequently when the catheter is inserted through scar tissue or bent acutely during insertion. To summarize, a primary reason for this undesirable characteristic is that the sheath material is forced outwardly from its close-fitting relation with the dilator unit during the insertion process, because the plastic material of the thin, tubular sheath lacks the desired hoop strength to avoid slight, undesired radial stretching at the distal tip during the insertion operation. However, many plastics which have higher hoop strengths are undesirably stiff, and thus would exhibit other disadvantages as a material for manufacturing a catheter introducer sheath.

In accordance with this invention, a catheter introducer sheath is provided which is highly flexible and strongly resistant to kinking, but also exhibits a surprisingly high hoop strength to avoid radially outward stretching of the distal tip thereof, despite the great overall flexibility of the tubular sheath. For example, with the preferred tubular sheath of this invention when it does not contain a catheter or dilator unit, it is possible to tie a loose, overhand knot in without kinking anywhere along the tubular sheath, so that the lumen remains open. This is quite impossible with the presently used catheter introducer sheaths. When it is attempted, the stiffer, prior art sheaths kink, collapsing the lumen at various positions, and often leaving a permanent crease in the sheath wall from the attempt.

DESCRIPTION OF THE INVENTION

In this invention, a catheter introducer is provided which comprises a tubular sheath for inserting and guiding a catheter into living tissue, typically a blood vessel of a patient. In accordance with this invention, the tubular sheath is made of expanded, fibrous polytetrafluoroethylene (PTFE), polyurethane, silicone, or polyethylene, polypropylene copolymers of polyethylene, or similar materials. As a result of this, the sheath may be highly flexible and non-kinking, but with relatively high hoop strength, so that the problem of notching, kinking, or burring at its distal tip during insertion thereof is strongly suppressed.

Preferably expanded PTFE is used. Such sintered, fibrous, expanded plastics are well-known materials and have been previously used in vascular grafts to protect a patient against aneurism. In such a role, expanded PTFE has been used as a permanent implant, but not as a removable catheter introducer sheath, which has very different technical requirements and functioning, when compared with a permanent implant. See the article by Michael E. McClurken et al. entitled Physical Properties and Test Methods for Expanded Polytetrafluoroethylene (PTFE) Grafts. Vascular Graft Update: Safety and Performance, ASTM STP 898, Helen E. Kambic et al., American Society for Testing and Materials, Philadelphia, 1986, pp 82-94.

Expanded fibrous PTFE and other plastic products are commercially available from a variety of sources. See also Gore U.S. Pat. Nos. 3,953,566 and 4,187,390, and see also Okita U.S. Pat. No. 4,082,893. As disclosed from such sources, expanded PTFE is a composite, porous, microfibrous form of PTFE which is generally flexible in nature. An expanded, fibrous polyurethane is sold by Monsanto under the trademark "SORBOTHANE".

The catheter introducers of this invention having tubular sheaths of preferably expanded PTFE may use sheaths which are of a length and a wall thickness similar to the corresponding sheaths of the prior art, with the remainder of the catheter introducer being also similar to prior art catheter introducers. Also, the expanded tubular PTFE and other plastic sheaths of this invention may be used in other forms of catheter introducers, or it may be used as a catheter itself, for example catheters for the vascular system or for any other desired catheter use.

The expanded PTFE and other plastic tubular sheaths of this invention can exhibit the desirable property that they resist stretching both longitudinally and radially, but they are correspondingly compressible to a significant degree in the longitudinal and radial directions, which facilitates their desirable combination of flexibility coupled with high hoop strength, particularly in the radially outward direction. Thus, despite their flexibility, the distal tips of the tubular sheaths used herein will adhere tightly and closely to a properly fitting dilator unit, to greatly suppress burring, notching or kinking. Additionally, the expanded plastic sheaths of this invention can exhibit good biocompatibility and low frictional characteristics, to facilitate their insertion through tissues. Preferably, the plastic materials used provide to the expanded, fibrous tubular sheaths of this invention a relatively high longitudinal and radial tensile strength coupled with a relatively low degree of stretching at the break point. Specifically, it is preferred for the maximum longitudinal tensile strength for the expanded plastic tubular sheaths of this invention to be at least 1,000 psi, and for the radial tensile strength to be at least 3,000 psi, with the elongation or longitudinal strain to break being no more than about 125 percent as described in the article by Michael E. McClurken et al. cited above, and expanded fibrous PTFE tube (IMPRA ® graft) having an inside diameter of 6.0 mm and a wall thickness of 0.81 mm and a specific gravity of 0.565 gram/cm$^3$ was tested as follows:

Longitudinal tensile strength was determined on a tubular graft sample of 57 mm in length and made of expanded PTFE is clamped between a pair of jaw grips and stretched at a constant rate of 6.35 mm/minute. The resulting force required to maintain this constant cross head speed is indicated on the recorder that is synchronized with an Instron tensile testing machine being used. The stress vs strain of such a PTFE fibrous tube reaches a maximum longitudinal tensile strength prior to break of about 1700 psi. At this maximum tensile strength the longitudinal strain is about 60 percent. For a determination of maximum radial tensile strength, a two centimeter piece of the fibrous PTFE tubing is placed over a split pair of curved pins that are mounted in an Instron tensile testing machine. The moving pin is driven at a constant speed of 25.4 mm/minute. The maximum radial tensile strength was 810 psi, and the radial strain about 600% at the sample break.

With respect to burst strength calculations of the same type of expanded PTFE tubing, as described in the McClurken et al. article the estimated peak pressure of 49.6 psi occurs at a radial dilatation or elongation of 33.3%. The pressure at actual burst is significantly less.

Accordingly, it can be seen that the fibrous expanded plastic materials may be quite flexible, but behave differently from simple elastomers, being more resistant to stretching while being very compliant and easily collapsed. By this invention the use of such materials as catheter introducer sheaths provides significant advantages as described herein.

The expanded, fibrous plastic tubular materials used in this invention are typically made by a sintering process, as is well-known in the art.

DESCRIPTION OF DRAWINGS

In the drawings FIG. 1 is a perspective view of a catheter introducer made in accordance with this invention;

FIG. 2 is an enlarged, exploded view, taken partly in longitudinal section, of the proximal end of the catheter introducer of FIG. 1;

FIG. 3 is a longitudinal sectional view of the proximal end of the catheter introducer of FIG. 1, showing the dilator unit in position;

FIG. 4 is an elevational view, with portions broken away, of the catheter introducer of FIG. 1 and the installed dilator unit in the process of being advanced into an artery of the patient; and FIG. 5 shows the catheter introducer of FIG. 1 after it has been so advanced into the artery of a patient, and the dilator unit and internal guide wire have been withdrawn, with an advancing catheter being shown.

DESCRIPTION OF SPECIFIC EMBODIMENT

Referring to the drawings, FIG. 1 shows a catheter introducer which is substantially identical to current, commercially available catheter introducers of the prior art, but for the modifications of this invention. Catheter introducer 10 comprises a tubular sheath 12 which carries a hub 14 at its distal end. Hub 14, in turn, contains a hemostasis valve 16 comprising a slotted rubber disk, which may be of any desired known design, and is particularly of the design disclosed in Hillstead allowed U.S. Pat. Application Ser. No. 194,539, filed May 16, 1988 and entitled Medical Instrument Valve now U.S. Pat. No. 4,895,565. Valve 16 provides sealing of sheath 12 around dilator unit 28, and later the catheter 36 which extends longitudinally through tubular sheath 12, to reduce blood loss.

Also, hub 14 defines a branch conduit 18, which carries on its outer end a three way valve for connection with a source of intravenous fluid or medicine, and also to measure arterial pressure as necessary, in a manner similar to the conventional use of catheter introducers. Conduit 18 is a flexible tube that fits in sliding manner over side port 19 of hub 14, and a locking sleeve 21 fits over the resulting assembly.

Hub 14 carries a sealed or snap-fit end cap 22, which, as shown, peripherally seals hemostasis valve disk 16 in a pressure seal formed between end cap 22 and hub 14.

In accordance with this invention, tubular sheath 12 may be made of expanded polytetrafluoroethylene, available for example from W. L. Gore and Associates Inc., with tubular sheath 12 being of a wall thickness and an outer diameter which is comparable to the tubular sheaths of the prior art. Specifically, tubular sheath 12 may have an inner diameter of 0.105 inch, a wall thickness of 0.015 inch and a length of about 4 inches. As previously described, such a tubular sheath, when unsupported by a catheter or dilator unit, is very flexible in terms of being non-self supporting, so that it can be limp and dangling rather than self supporting through its own internal strength. Nevertheless, tubular sheath 12 exhibits a substantial amount of hoop strength resistance against internal collapse, and when it does collapse it does so without kinking, in that it can be restored to its original form while typically not leaving any creases to show the bending.

Even more so, the tubular sheath of this invention exhibits very strong hoop strength resistance against radial longitudinal stretching. While sheath 12 is very flexible, and thus very unlikely to cause tissue injury when installed in the arteriovenous system, it is also very resistant to stretching, particularly in the radial direction. This greatly reduces the possibility of the distal end of sheath 12 forming a burr, a notch, or a kink as it is advanced as in FIG. 4 through the tissue of the patient. The distal end 26 of sheath 12 thus can form a tight, non-stretchable sleeve about its dilator unit 28 to avoid the above-stated undesirable phenomena.

Dilator unit 28 may be of conventional design, and is shown in FIG. 3 after its insertion into the catheter introducer as extending through hemostasis valve 16 in sealing manner, and also through tubular sheath 12 in typically snug-fitting manner. Because of the inherent lubricity of expanded PTFE, the inner diameter of sheath 12 may be made essentially identical to the outer diameter of dilator unit 28, and the dilator unit can still be advanced through the sheath with low friction.

As shown in FIG. 4, the catheter introducer of this invention is shown in one step of a process for inserting an angiographic catheter into an artery 32 of a patient. In FIG. 4, guide wire 30 has already been inserted into the artery in a conventional manner, which is basically described in the previously cited Stevens patent. Catheter introducer 10, carrying its dilator unit 28 as shown in FIG. 4, is about to be pressed through the aperture 34 into artery 32, to stretch the aperture while providing minimal opportunity for unlimited bleeding. First, the distal tip 29 of dilator unit 28 is inserted through aperture 34, followed by distal end 26 of sheath 12 carried on dilator unit 28, for installation of catheter introducer 10.

Then, as a subsequent step, FIG. 5 shows how a catheter 36 can be inserted through sheath 12 of the emplaced catheter introducer, after removal of dilator unit 28 and guide wire 30, for the desired emplacement of catheter 36 in the artery for conventional purposes of angiography or any other desired purpose. Because tubular sheath 12 is made of expanded PTFE, the advancement of catheter 36 through the lumen thereof can be accomplished with relatively low friction and ease. Also, because of particularly the flexibility coupled with the hoop strength of tubular sheath 12, the disadvantages of prior art catheter introducers may be avoided, so that the catheter introducer of this invention exhibits significant advantages over those of the prior art.

The above has been offered for illustrative purposes only, and is not intended to limit the scope of the invention of this application, which is as defined in the claims below.

That which is claimed:

1. A catheter introducer adapted to be temporarily introduced into a patient's blood vessel, said catheter introducer comprising a hub containing a hemostasis valve and a tubular sheath substantially longer than said hub, said sheath being adapted to enclose a dilator which has an end which extends forward of the end of the tubular sheath when the dilator is inserted within the catheter introducer for introduction of the dilator and the tubular sheath into a patient's blood vessel, with the dilator thereafter being removed from the introducer to enable the introducer to receive a catheter, said elongated, tubular sheath being made of an expanded, fibrous plastic, whereby said sheath is highly flexible and non-kinking, but with relatively high hoop strength.

2. The catheter introducer of claim in which said hub defines a branched conduit and a central conduit, both conduits communicating with the lumen of said tubular sheath.

3. A catheter introducer adapted to be temporarily introduced into a patient's blood vessel, said catheter introducer comprising a hub containing a hemostasis valve and a tubular sheath substantially longer than said hub, said sheath being adapted to enclose a dilator which has an end that extends forward of the end of the tubular sheath when the dilator is inserted within the catheter introducer, for introduction of the dilator and the tubular sheath into a patient's blood vessel with the dilator thereafter being removed from the introducer to enable the introducer to receive the catheter; said elongated, tubular sheath being made of expanded, fibrous polytetrafluoroethylene whereby said sheath is highly flexible and non-kinking, but with relatively high hoop strength.

4. The catheter introducer of claim 3 in which said hub defines a branched conduit and a central conduit, both conduits communicating with the lumen of said tubular sheath.

5. In the method of inserting a catheter into the arteriovenous system of a patient including the steps of inserting a distal portion of a catheter introducer sheath which contains a dilator unit into the arteriovenous system, removing the dilator unit, and inserting said catheter through the catheter introducer sheath into the arteriovenous system, the improvement comprising:

said catheter introducer sheath being made of expanded, fibrous plastic, whereby said sheath is highly flexible and non-kinking, but with relatively high hoop strength.

6. The method of claim 5 in which said catheter is inserted into an artery for angiography.

7. The method of claim 5 in which said expanded, fibrous plastic is polytetrafluoroethylene.

* * * * *